United States Patent
Nicolaus

(10) Patent No.: US 9,510,791 B2
(45) Date of Patent: Dec. 6, 2016

(54) DIAGNOSTIC EFFICIENCY

(71) Applicant: SymCollect GmbH, Langerringen (DE)

(72) Inventor: Carsten Nicolaus, Augsburg (DE)

(73) Assignee: SYMCOLLECT GMBH, Langerringen (DE)

( * ) Notice: Subject to any disclaimer, the term of this patent is extended or adjusted under 35 U.S.C. 154(b) by 65 days.

(21) Appl. No.: 14/564,822

(22) Filed: Dec. 9, 2014

(65) Prior Publication Data
US 2016/0157789 A1 Jun. 9, 2016

(51) Int. Cl.
*G08B 23/00* (2006.01)
*A61B 5/00* (2006.01)
*G06F 19/00* (2011.01)

(52) U.S. Cl.
CPC ............ *A61B 5/747* (2013.01); *A61B 5/0022* (2013.01); *G06F 19/3418* (2013.01); *G06F 19/363* (2013.01); *A61B 5/4836* (2013.01); *A61B 5/4842* (2013.01)

(58) Field of Classification Search
CPC ......... G06F 19/36; G06F 19/00; G06F 19/322
USPC ............. 340/573.1; 705/2, 3; 709/203, 217; 715/234; 600/300, 500, 565, 529
See application file for complete search history.

(56) References Cited

U.S. PATENT DOCUMENTS

| | | | | |
|---|---|---|---|---|
| 7,603,282 B2* | 10/2009 | Imai | ...................... | G06Q 30/02 705/2 |
| 2002/0035486 A1* | 3/2002 | Huyn | .................. | G06F 19/3418 705/3 |
| 2002/0133377 A1* | 9/2002 | Brown | ................ | G06F 19/3418 705/3 |
| 2003/0028399 A1* | 2/2003 | Davis | .................... | G06F 19/327 705/2 |
| 2005/0256379 A1* | 11/2005 | Matory | ................ | A61B 5/0002 600/300 |
| 2012/0130742 A1* | 5/2012 | Church | .................. | G06Q 50/24 705/3 |
| 2012/0277543 A1* | 11/2012 | Homchowdhury | .. | A61B 5/0022 600/300 |

* cited by examiner

*Primary Examiner* — Toan N Pham
(74) *Attorney, Agent, or Firm* — Paul D. Bianco; Fleit Gibbons Gutman Bongini & Bianco PL

(57) ABSTRACT

Doctor and patient communication is improved by electronically transmitting a series of questions to a computing device of the patient, and electronically receiving answers to the questions provided by the patient. A computer server analyzes the answers to the questions to determine if a state of health of the patient is serious and requires the immediate attention of the doctor. If the software determines the state of health to be serious, the server transmits an alert to a computing device of the doctor. The alert can include a series of lights, for example in the form of a traffic light, to quickly convey to the doctor the state of health of the patient.

20 Claims, 3 Drawing Sheets

DIAGNOSTIC EFFICIENCY

FIELD OF THE DISCLOSURE

The disclosure relates to a system and method for improving communication between a doctor and patient, and more particularly, electronic realtime communication with prompted input from the patient.

BACKGROUND OF THE DISCLOSURE

A clinical decision support system (CDSS) is a computer based system health professionals with decision making, including diagnosis of patient data. Such systems can use artificial intelligence and learning, or a knowledge base. Typically, the CDSS provides suggestions which are interpreted by the doctor. The systems include a knowledge base, an inference engine, and a mechanism to communicate. The inference engine combines the rules from the knowledge base with the patient's data. The communication mechanism allows the system to show the results to the user as well as to enable the user to input data. Examples include Isabel, Caduceus, DiagnosisPro, and DXplain. CDSS systems enable the user to enter information pertaining to symptoms, and the system responds with a list of possible diagnoses.

A variety of devices are available for patients who are at risk of falling or otherwise becoming unable to move to summon help. Such devices include pull-cords connected to fixed devices, and wireless transmitters that can be worn by the patient, and that include a push button to transmit an alert. Sensors such as electronic pads and belts can indicate when a patient has moved from a safe location.

Pagers and cell phones can be used by patients to summon help, or to call a medical practitioner for advice. Email and text messaging can also be used by patients to communicate with a doctor or medical practitioner.

SUMMARY OF THE DISCLOSURE

A method of improving doctor and patient communication, comprises electronically transmitting a series of questions to a computing device of the patient; electronically receiving answers to the questions, provided by the patient, from the computing device of the patient, by a computer server; executing software stored on non-transitory media connected to the computer server, the software configured for analyzing the answers to the questions to determine if a state of health of the patient is serious and requires the immediate attention of the doctor; and if the software determines the state of health is serious, transmitting an alert, using the server, to a computing device of the doctor.

In an embodiment thereof, the method further includes electronically transmitting the received answers from the server to the computing device of the doctor.

In various other embodiments thereof, a determined state of health of serious corresponds to a third state of health, the software further configured to analyze the answers to the questions to determine if a first state of health of the patient is below a predetermined threshold corresponding to a satisfactory state, or a second state of health of the patient is between the thresholds of the first and third states of health corresponding to a worsening state of health; and/or the computing device of the doctor is configured to execute software stored on non-transitory media, the software configured to display a visible alert, upon a display of the computing device of the doctor, in the form of a series of different colored lights to indicate a state of health of the patient corresponding to each of the third, second, and first states of health, respectively; the method further comprising indicating, using the visible alert to display a colored light corresponding to the determined state of health of the patient.

In other embodiments thereof, the computing device of the doctor is configured to execute software stored on non-transitory media, the software configured to display a visible alert, upon a display of the computing device of the doctor, in the form of red, yellow, and green lights, to indicate a state of health of the patient corresponding to the third, second, and first states of health, respectively; the method further comprising indicating, using the visible alert, a red, yellow, or green light corresponding to the determined state of health of the patient. In addition or in the alternative, the computing device of the patient is configured to execute software stored on non-transitory media, the software configured to display a visible alert, upon a display of the computing device of the patient, in the form of red, yellow, and green lights, to indicate a state of health of the patient corresponding to the third, second, and first states of health, respectively; the method further comprising indicating, using the visible alert, a red, yellow, or green light corresponding to a current state of health of the patient.

In a further embodiment thereof, at least one of the computing device of the patient or the doctor is configured to execute software stored on non-transitory media, the software configured to display a visible alert, upon a display of the computing device of the patient or doctor, in the form of traffic light having red, yellow, and green lights, to indicate a state of health of the patient corresponding to the third, second, and first states of health, respectively; the method further comprising indicating, using the traffic light visible alert, a red, yellow, or green light corresponding to a current state of health of the patient.

In still further embodiments thereof, the software is further configured to generate reports for the patient and the doctor based upon the analysis of the answers to the questions; and the method further includes generating the reports for the patient and the doctor;

the report for the patient and the doctor are different;

the software is further configured to generate a report for the doctor, the report based upon the analysis of the answers to the questions, the report further including information not provided by the patient that is relevant to the analyzed state of the patient; the method further including transmitting the generated report to the doctor;

the computing device of the patient is configured to execute software stored on non-transitory media, the software configured to prompt the patient to answer a subset of questions of the series of questions based on previous answers to questions of the series of questions; the method further including prompting the patient to answer the subset of questions;

the computing device of the doctor is configured to execute software stored on non-transitory media, the software configured to generate a series of questions responsive to the received answers and data input from the doctor; the method further including generating the series of questions and transmitting the generated series of questions to the patient;

the computing device of the doctor is configured to execute software stored on non-transitory media, the software configured to display, upon a display of the computing device of the doctor, information pertaining to contacting the patient; the method further including displaying the information pertaining to contacting the patient when the state of health of the patient is serious.

the series of questions includes questions pertaining to at least one of a family life of the patient; a job and workplace of the patient; and an engagement by the patient in sport and exercise;

the series of questions includes questions pertaining to at least one of side effects of any current medications of the patient; and allergies of the patient; and/or the series of questions include questions pertaining to physical symptoms of the patient;

the software is further configured to generate statistics relevant to the answers to the questions, the statistics indicating a state of health of the patient relative to a population of a plurality of patients with similar symptoms; the method further including communicating the statistics to the patient using the computing device of the patient.

In another embodiment of the disclosure, a method of improving doctor and patient communication, comprises electronically transmitting a series of questions to a computing device of the patient; electronically receiving answers to the questions from the computing device of the patient by a computer server; executing software stored on non-transitory media connected to the computer server, the software configured for analyzing the answers to the questions to—determine if a state of health of the patient is serious and requires the immediate attention of the doctor, and determine a new series of questions to be transmitted to a computing device of the patient, the new series of questions derived from the received answers to question; and if the software determines the state of health is serious, transmitting an alert, using the server, to a computing device of the doctor.

In an embodiment thereof, at least one of the computing device of the patient or the doctor is configured to execute software stored on non-transitory media, the software configured to display a visible alert, upon a display of the computing device of the patient or doctor, in the form of a series of at least three different colored lights, to indicate a state of health of the patient corresponding to the serious state of health of the patient, a worsening state of health of the patient, and a non-serious state of health of the patient, respectively; the method further comprising indicating, using the visible alert, a colored light corresponding to the determined state of health of the patient.

In a further embodiment of the disclosure, a system for improving doctor and patient communication, comprises a computer server configured to execute software stored on non-transitory media, the software configured for: electronically receiving answers to questions provided by the patient, from a computing device of the patient; executing software stored on non-transitory media connected to the computer server, the software configured for analyzing the answers to the questions to determine if a state of health of the patient is serious and requires the immediate attention of the doctor; and if the software determines the state of health is serious, transmitting an alert, using the server, to a computing device of the doctor.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE DISCLOSURE

Figure 1:
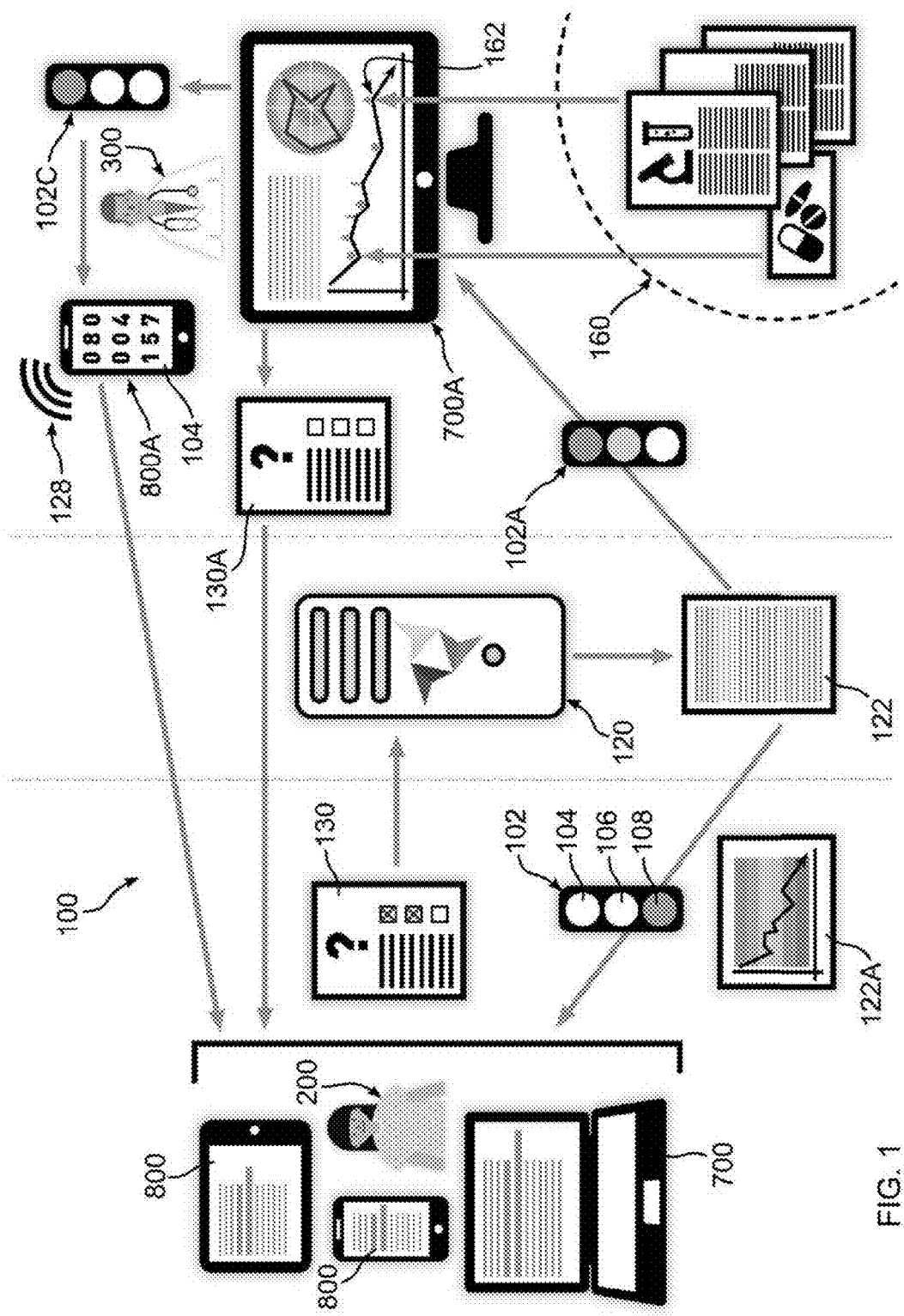
FIG. 1 is a diagrammatic view of communication between a patient and a doctor, in accordance with the disclosure.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

A relationship between an attending doctor, medical practitioner, or medical staffperson (hereinafter, doctor) and a patient is a very important factor in the healing process, especially in chronic illnesses and during long-term treatments. The doctor needs regular feedback about the patient's condition, and patients often wish attention and ideally the continuous presence or availability of the doctor.

In an embodiment of the disclosure, a computer software application 110 is provided, the application configured to execute upon a computing device 700 (FIG. 2) operable by the patient or the patient's caregiver if the patient is unable. The patient uses the software to input vital signs, symptoms, environmental data, and other relevant information, for electronic transmittal to the doctor for evaluation. The software enables the patient to communicate more efficiently and effectively with their doctor.

The computing device can be a wireless or mobile computing devices 800 (FIG. 3), for example a smartphone or tablet, which can be used to enable the patient to provide input conveniently at predetermined time periods throughout the day, although a desktop or terminal can also be used for this purpose.

Computer connectable devices 742 (FIG. 2) which are able to measure and transmit physiological data can be used to capture and transmit, for example, body temperature or arterial pressure, and audio or video data of the body, and can interface with software of the disclosure to increase accuracy and convenience for the patient in reporting important patient data. Patients can also collect physiological data using the various well known non-computer enabled devices, and enter this information using the software. In one embodiment, the patient or its designee provides written responses to a questionnaire 130. In another embodiment, audio and/or video data is captured of the patient answering questions, the audio and video data being viewable by the doctor remotely in real time or at a later time.

In another embodiment, software 110 executing upon the patient's computing device prompts the patient to answer certain questions of the questionnaire based on previous responses to questions of the questionnaire. In this manner, the patient only answers questions which are relevant based upon all of the questions the patient has answered.

The doctor can receive this input data directly from the patient on a computing system operated by the doctor, via a computing network 795, for example the internet, at predetermined intervals, for example daily, or as the data is entered. A regular update of the patient's condition and symptoms enables the doctor to closely follow the patient's evolving condition, and to take action when needed. When the input data corresponds to any of a variety of critical health parameters, the software can produce an automatic alarm which activates to notify the doctor more quickly. The patient, too, can receive feedback on the progression of his healing process, for example in the form of easily understandable graphs or visuals, which do not require advanced medical training to understand. System 100 can be configured to enable the doctor to decide whether or not to provide feedback to the patient using system 100, or whether or not to enable the patient to contact the doctor directly.

A computer server 120/700 can be connected to the network to gather, store, forward, and analyze input data from one or many patients. Collectively, the server 120, the patient's computing device 700/800, and the doctor's computing device 700/800 form a system 100 of the disclosure. Software 110 includes software components executable on any or all of the patient, doctor, and server computing devices. Server 120 can form a central repository and processing point for patient and doctor generated data, so that all patient's and doctor's receive the latest versions of questionnaires, data interpretation, and other system related data. In an embodiment, software 110 is configured to function as a clinical decision support system (CDSS). Portions of the CDSS can be configured to execute on a computing device of the patient, the server, or a computing device of the doctor. The CDSS can be configured to analyze answers to the questionnaire by the patient, and/or to analyze answers as modified by the doctor. In another embodiment, the CDSS results are interpreted by the doctor prior to a determination of a status condition of the patient, and issuance of an alert by system 100 of the disclosure.

In an embodiment, patients voluntarily submit their data, for example on an anonymous basis, so that collective results can be analyzed to improve diagnostic results and outcomes for all patients. This data collection can be particularly useful for analyzing information from the course of long term diseases, and for studies and research purposes. Because each patient can input data on a daily or other frequent and regular basis, considerably more data is generated than would be collected, for example, only during doctor's office visits. This vast collection of data can provide new insights into the various disease processes and treatments, the amount of data being heretofore unavailable, even from large clinical studies.

Software of the disclosure incorporates simple or extensive surveys or questionnaires which the patient can respond to, in order to collect useful health related information. On a daily or predetermined time basis, the patient answers designated questions about their condition or illness, using their computing device. Answers from the previous day can be shown in context to facilitate the patient in providing consistent and accurate responses. Questions can relate to: typical symptoms of a suspected or known illness and its characteristics; possible therapeutic side effects of a course of treatment the patient is undergoing; allergic reactions the patient may be experiencing; key environmental factors; and the patient's general state of health. Sample questions are illustrated in Table 1.

TABLE 1

Sample Questionnaire Excerpts

Base Data

| | |
|---|---|
| General practitioner | xxxxxxxxxxxxxx |
| Specialist | xxxxxxxxxxxx |
| Clinic | xxxxxxxxx |
| Patient Gender | F |
| Current therapy | xxxxxxxxxxxxxxxxxxxxxxxxxxxxx |

Daily Questionnaire
private and family situation

| | |
|---|---|
| serious trouble | 2 |
| the usual ups and downs | 1 |
| all is well | 0 | job and workplace

| | |
|---|---|
| stress level and workload above average | 2 |
| normal workload | 1 |
| stress level and workload below average | 0 |
| holidays/I don't work (currently) | 0 | sport and exercise

| | |
|---|---|
| very little | 2 |
| less than average | 1 |
| within average range | 0 |
| markedly more/more demanding than usual | 0 |

Side effects by current therapy
acute allergic symptoms current

| | |
|---|---|
| do not know | 0 |
| no | |

Allergy type

| | |
|---|---|
| local itching | 2 |
| general itching | 5 |
| local wheals | 2 |
| general wheals (Urtikaria) | 10 |
| local rash | 2 |
| general rash | 5 |
| swelling of the tongue | 10 |
| shortness of breath | 10 |

Stomach pains current

| | |
|---|---|
| entire stomach | 5 |
| locally | 2 |
| never | 0 |

Exhaustion/fatigue current/recent

| | |
|---|---|
| strong | 5 |
| medium | 3 |
| slight | 1 |
| none | 0 |

Global Remarks
Questionnaire Completed

At the end of the survey, the patient can receive a statistical evaluation in the form of several graphs or other visual representations on the patient's computing device.

Data presented can include information pertaining to the development of the general condition according to fundamental factors, for example including a spider diagram of the condition according to various categories.

When certain previously defined border values show a worsening of the patient's condition, the doctor receives an automatic alert, generated by system 100, by email, text, or other mode. Once the doctor becomes aware of a serious condition, the doctor can avail himself of an immediate feedback channel provided by system 100 between the doctor and patient. More particularly, a messaging interface can be provided by software 110, which enables instant text chat, voice communication, or video communication between the patient and doctor. For less serious conditions, or where bandwidth or the patient's computing device is limited, other forms of communication can be used, for example email. As such, system 100 enables at least the following:

intensification of the doctor/patient relationship as needed during periods of serious or chronic illness, or during periods of long-term care, where symptoms and progression of the illness or treatment can be evaluated more closely;

improved coaching between a specialist and an attending practitioner is possible in real time, where the specialist is also able to see the patient's data and/or receives alerts; and scientific assessment of progression and success of treatments in chronic illnesses, by aggregation of anonymous data, which can be used by health institutions, research organizations and companies which are consumers of health related data.

System 100 further provides opportunities for optimized therapy by doctors and health improvement facilities due to, for example:

continuous patient monitoring, and an automatic alert or red flag system in cases of drastic worsening of the patient's condition;

less dependency on intermittent and subjective descriptions of symptoms, by using objective patient data based upon routine data collection;

availability of historical objective data, for example data from previous weeks, months, or years, which can be considered, for example, prior to a patient appointment; and the possibility to make notes and remarks that are accessible as selectively authorized, to allow a simplified control of successful therapeutic/medicamentous measures by multiple medical practitioners.

System 100 helps patients, by providing the following, for example: diary functions; constant monitoring of critical parameters via an automatic alert function; a sense of security; objective information about a successful therapy; independent observation of healing progress or setbacks; recognizing and identifying helpful or counterproductive behavior; enabling doctors to provide patients with relevant information.

With respect to the diary function, a patient can benefit from the recording of health parameters, whether or not those parameters will be transmitted to a doctor. For example, this information can be useful in building an accurate case history for the patient. This can be particularly important if the patient suffers from poor memory. As system 100 prompts the patient, key information can be obtained which the patient may not think to record, or may not be aware is important to a future diagnosis of their health. Accordingly, system 100 can be configured to enable a standalone diary feature, with or without data collection and/or analysis at the server, and with or without an interface to a doctor.

System 100 can be particularly effective for diagnosing and treating multi-system illnesses, and multi-infectious disease syndrome. One example is the diagnosis and treatment of tick-borne diseases, such as chronic transmissible Lyme disease. As described elsewhere herein, a mental and physical status questionnaire is completed by the patient and analyzed by one or more doctors, using system 100. After analysis of the data, the patient can receive a regular, for example weekly, report of his daily input. In case of important changes of the patient's status, the doctor can receive immediate relevant information.

In an embodiment, one or more of the doctors responsible for a patient can change the questions in the questionnaire. The doctor can additionally change the set points for automatic alarms, based on knowledge of the particular patient's history that is available within system 100. System 100 can produce a statistical analysis, or provide the needed data to prepare a statistical analysis, which can be a useful tool in the control, documentation, or adoption of an effective therapy. The statistical analysis can further illustrate a relative success of various medications or alternative therapies.

System 100 can be used for therapeutic treatment in a variety of medical fields, including, for example, oncology, diabetes, pain, cystic fibrosis/mucoviscidosis, urology, and research.

In an embodiment, an application embodying software 110 can be provided to patients free of charge, and the patient, doctor, insurer, government, or health care company can pay the costs associated with ongoing data collection, storage, and analysis. For example, a freely cancellable monthly fee can be used to collect patient information; provide a weekly statistical evaluation of the data collected and reported to the doctor and patient; provide an alarm function, if medically necessary; provide additional statistical functions needed by the doctor; and provide secure and anonymous data storage. Other modes of financing the ongoing operation of system 100 can be used. It should be understood that use of system 100 should not replace regular in-person visits with a doctor, if this is possible.

With reference to FIG. 1, vertical dotted lines delineate actions which relate to the patient's computing device at left, the server, in the middle, and on the doctor's computing device, at right. In an embodiment of the disclosure, a traffic light 102 is used to quickly convey a patient's health status. One or more traffic lights, each depicting 3 colors—red 104, yellow or amber 106, and green 108—is displayed on the patient's and the doctor's computing device. In one embodiment, only one color is 'lit', brightened, or otherwise indicated at one time. In other embodiments, more than one light can be indicated, for example to indicate a midpoint condition. The traffic light metaphor enables the patient or doctor to quickly see the patient's status, where a red light indicates that the patient is experiencing a serious condition requiring further attention; a yellow light indicates the patient's health is worsening, or trending in an unhealthy direction, or the patient is somewhat at risk of a more serious condition; and green indicates the patient's condition is normal or non-serious. Each of the three conditions can be indicative of that particular condition for an individual patient. More particularly, a set of physiological conditions for one patient which is 'green', or normal, may correspond to a 'yellow' or 'red' condition for another patient.

It should be understood that a series of lights of any color can be used to convey a status of the patient, and the lights can be displayed alone, and not associated with a recognizable object such as a traffic light. For example, in various cultures, other colors or objects may be better recognized to readily convey a non-serious, worsening, or serious state by analogy to a routinely observed system of colors and conditions.

With further reference to FIG. 1, a patient 200 completes an electronic questionnaire 130 using a computing device 700/800, which is electronically forwarded by the computing device using any known means to server 120. It should be understood that the disclosure can be carried out by directly transmitting the survey and/or any other communication from the patient directly to the doctor's computer, bypassing server 120. However, when server 120 is used, data can be collated and analyzed more efficiently. Further, if the doctor or the patient do not have their respective computers running, server 120 can hold any transmitted data until the recipient computer is able to receive the data.

In the embodiment of FIG. 1, server 120 produces a report 122 in any known or hereinafter developed format, for example a diagrammatic format, which is forwarded to both the patient and the doctor. The report represents at least a portion of the data input on the questionnaire by the patient, as well as related data, for example a suggested diagnosis or treatment, or information pertaining to a diagnosis or treatment of other patients with similar symptoms. The report 122, 122A prepared for the doctor and patient, respectively, can be different, the contents of each targeted to a knowledge level and sensitivity of each recipient. The report itself, or one or more portions of the report, may have a traffic light associated with it. In FIG. 1, light 102 has the green light indicated, although any other light could be indicated, based upon the associated information. In an embodiment, only 'green' or positive information is contained on the report for the patient, as warning or danger conditions corresponding to yellow or red lights may need to be communicated to the patient in a different manner. In the example shown, there are red and yellow portions of the report, which correspond to yellow and red conditions of the patient. Accordingly, the red and yellow traffic lights are highlighted in light 102A, which is visible on the doctor's computing device. In this manner, the doctor 140 is quickly made aware of these conditions, and can take timely and appropriate action.

A computing device 700A of the doctor 300 can be used by software 110 to display a visual indication of the patient's history, together with any diagnostic imaging or other information relevant to the patient's condition. The information can be forwarded to the doctor's computer from server 120. While a desktop display is illustrated in FIG. 1, it should be understood that the doctor could view this information on a portable or mobile device, which can enable monitoring by the doctor while making rounds, or otherwise when the doctor is away from his desk.

As further illustrated in FIG. 1, information from lab reports, scientific publications, therapeutic drug information, and other relevant information 160 can be selected by software 110 and made available to the doctor when reviewing a patient's data Links or icons 162 can be placed at appropriate points within a visual display of patient data, each link associated with one or more items of relevant information 160. In this manner, the doctor can quickly understand the patient's condition, and can access related information that may be useful in understanding the patient's condition, and possible courses of treatment. Information 160 can additionally or alternatively be supplied by server 120.

Traffic light 102C can be displayed on a smartphone 800A or other computing device that the doctor always carries. In this manner, any 'red' light or serious changes in condition of the patient can be brought to the attention of the doctor as an alarm or alert. The carried computing device of the doctor can vibrate and/or sound an audio alert 128, in addition to displaying the traffic light indicating a red color. It should be understood that any other form of visual alert, instead of or in addition to the traffic light, may be displayed upon the patient or doctor's computing device. The doctor's computing device 800A can display information pertaining to the patient's condition, and can additionally display the patient's contact information, for example a phone number, so that the doctor can quickly contact the patient or a caregiver, in order to address a serious change in the patient's status.

In an embodiment of the disclosure, the doctor uses software 110 to generate questionnaires 130A, which may be any of new patient questionnaires, changes to a patient questionnaire, or a follow up questionnaire in response to a patient's answers to a previous questionnaire. In urgent cases, a doctor generated questionnaire can be transmitted directly to the patient's computing device, or the doctor generated questionnaire can be sent through server 120 to a particular patient, or numerous patients who are similarly situated.

The disclosure provides a service function for the doctor, who is alerted as soon as values of the sick patient go beyond certain predetermined limits. Because the patient knows that the doctor will be alerted when their medical parameters become critical, the patient will not need to contact his doctor as often as before. The patient additionally experiences greater peace of mind, improving their overall state of health. System 100 of the disclosure can further collect and store data over a long period of time, which data can be evaluated by doctors and experts to improve future results for patients.

Software 110 can provide or coordinate with realtime messaging systems on the patient and doctor's mobile or desktop computing device, so that timely communication and action can be established. Questionnaires, which may contain only a few questions, or many questions, can be created by: a doctor assigned to the patient's care; other doctors; computer software, for example artificially intelligent medical diagnostics software, or software associated with a medical diagnostics knowledge base; a combination of software and one or more doctors.

In an embodiment, patterns of patient symptoms, for example as indicated on numerous questionnaires by numerous patients, can be used by system 100 to determine epidemiological events which could affect a population at large. Examples include the spread of infectious disease. In an embodiment, patient data, possibly stripped of patient identifying data, can be sent to a disease management authority, for example the CDC, for evaluation and appropriate action. In addition to responding to questionnaires, patients can be provided with equipment which monitors one or more vital signs of the patient, and transmits this data automatically through system 100 to server 120, and as needed or requested, to the doctor. Other parameters of patient health can be monitored electronically, or values can be input by the patient or caregiver, including blood glucose, immunoassay results, blood gas, and other parameters. The doctor can view these results as they are input or acquired, particularly when an alert condition is indicated by system 100, or at regular intervals, and can diagnose the patient's condition, using all input data, either without the aid of computer diagnostics, or in combination with computer diagnostics.

In an embodiment, a computer in communication with the patient's computing device, or server 120, analyzes some or all of a patient's data, including physiologically sensed data and patient answers to questions, and determines a state of the patient's health. This determination can be used to determine an indicated color for one or more traffic lights of system 100, and to otherwise alert a doctor if the patient's condition appears to have become serious.

The disclosure enables the patient to avoid waiting in the doctor's office, or having to leave their home which may be difficult, and which could possibly expose others to their illness, while simultaneously enabling the doctor to communicate with the patient quickly when truly needed. Further, a frequency of doctor's office visits can be reduced, while patient care can be improved. Additionally, care for all people is improved, as detailed health related data is gathered from a large population in real time. The disclosure thus improves communication between patients and doctors, and thereby improves the efficiency of diagnosis, reducing illness and saving patient lives.

Example Computer System

Figure 2:
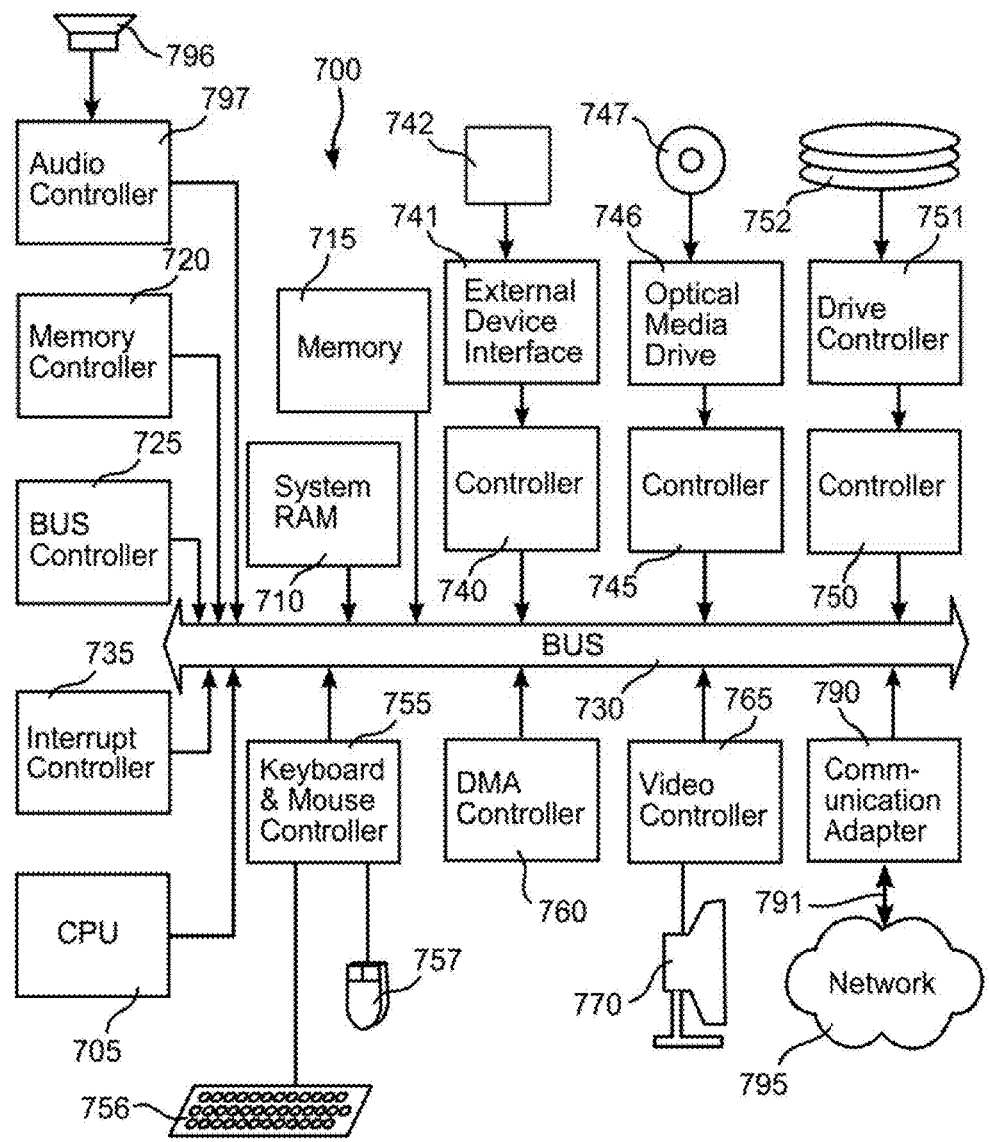
FIG. 2 is an illustrative computing system, with which one or more portions of the disclosure can be carried out.

FIG. 2 illustrates the system architecture for a computer system 700, such as a process controller, or other processor on which or with which portions of the disclosure may be implemented. The exemplary computer system of FIG. 2 is for descriptive purposes only. Although the description may refer to terms commonly used in describing particular computer systems, the description and concepts equally apply to other systems, including systems having architectures dissimilar to FIG. 2. Computer system 700 can control medical equipment, using for example actuators and transducers. One or more sensors, not shown, provide input to computer system 700, which executes software 110 stored on non-volatile memory or other media, the software configured to received inputs from sensors or from human interface devices, in calculations for controlling system 100.

Computer system 700 includes at least one central processing unit (CPU) 705, or server, which may be implemented with a conventional microprocessor, a random access memory (RAM) 710 for temporary storage of information, and a read only memory (ROM) 715 for permanent storage of information. A memory controller 720 is provided for controlling RAM 710.

A bus 730 interconnects the components of computer system 700. A bus controller 725 is provided for controlling bus 730. An interrupt controller 735 is used for receiving and processing various interrupt signals from the system components.

Mass storage may be provided by DVD ROM 747, or flash or rotating hard disk drive 752, for example. Data and software, including software 400 of the disclosure, may be exchanged with computer system 700 via removable media such as diskette, CD ROM, DVD, Blu Ray, or other optical media 747 connectable to an Optical Media Drive 746 and Controller 745. Alternatively, other media, including for example a media stick, for example a solid state USB drive, may be connected to an External Device Interface 741, and Controller 740. Additionally, a device 70 in accordance with the disclosure may be connected to computer system 700 through External Device Interface 741, for example by a USB connector, BLUETOOTH connector, Infrared, or WiFi connector, although other modes of connection are known or may be hereinafter developed. A hard disk 752 is part of a fixed disk drive 751 which is connected to bus 730 by controller 750. It should be understood that other storage, peripheral, and computer processing means may be developed in the future, which may advantageously be used with the disclosure.

User input to computer system 700 may be provided by a number of devices. For example, a keyboard 756 and mouse 757 are connected to bus 730 by controller 755. An audio transducer 796, which may act as both a microphone and a speaker, is connected to bus 730 by audio controller 797, as illustrated. It will be obvious to those reasonably skilled in the art that other input devices, such as a pen and/or tablet, Personal Digital Assistant (PDA), mobile/cellular phone and other devices, may be connected to bus 730 and an appropriate controller and software, as required. DMA controller 760 is provided for performing direct memory access to RAM 710. A visual display is generated by video controller 765 which controls video display 770. Computer system 700 also includes a communications adapter 790 which allows the system to be interconnected to a local area network (LAN) or a wide area network (WAN), schematically illustrated by bus 791 and network 795.

Operation of computer system 700 is generally controlled and coordinated by operating system software, such as a Windows system, commercially available from Microsoft Corp., Redmond, Wash. The operating system controls allocation of system resources and performs tasks such as processing scheduling, memory management, networking, and I/O services, among other things. In particular, an operating system resident in system memory and running on CPU 705 coordinates the operation of the other elements of computer system 700. The present disclosure may be implemented with any number of commercially available operating systems.

One or more applications, such as an HTML page server, or a commercially available communication application, may execute under the control of the operating system, operable to convey information to a user.

Example Mobile Computing System

Figure 3:
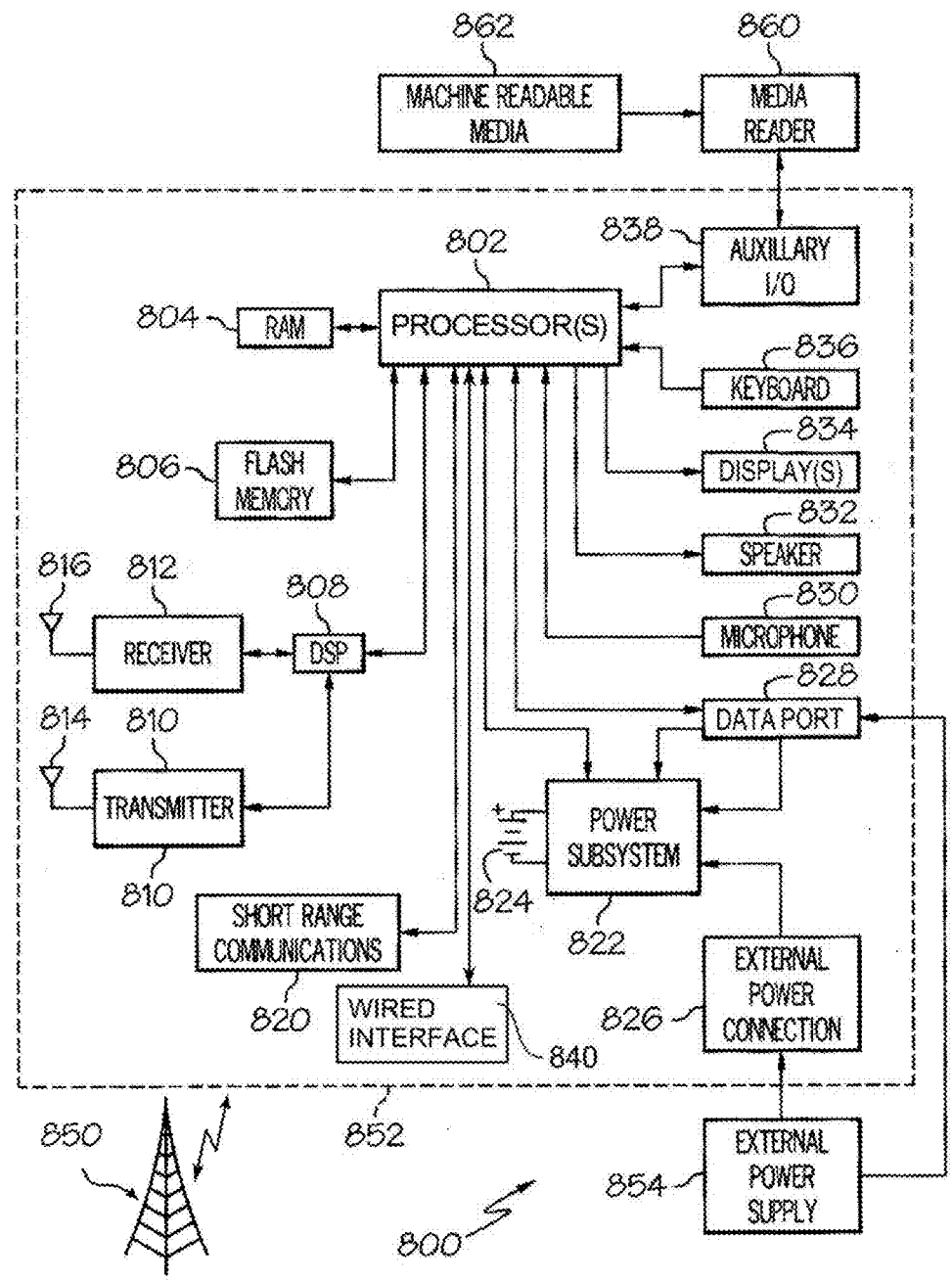
FIG. 3 is an illustrative mobile computing device, with which one or more portions of the disclosure can be carried out.

FIG. 3 is a block diagram of an electronic device and associated components 800, which can be used in carrying out portions of the disclosure. In this example, an electronic device 852 is a wireless two-way communication device with voice and data communication capabilities. Such electronic devices communicate with a wireless voice or data network 850 using a suitable wireless communications protocol. Wireless voice communications are performed using either an analog or digital wireless communication channel. Data communications allow the electronic device 852 to communicate with other computer systems via the Internet. Examples of electronic devices that are able to incorporate the above described systems and methods include, for example, a data messaging device, a two-way pager, a cellular telephone with data messaging capabilities, a wireless Internet appliance or a data communication device that may or may not include telephony capabilities.

The illustrated electronic device 852 is an example electronic device that includes two-way wireless communications functions. Such electronic devices incorporate communication subsystem elements such as a wireless transmitter 810, a wireless receiver 812, and associated components such as one or more antenna elements 814 and 816. A digital signal processor (DSP) 808 performs processing to extract data from received wireless signals and to generate signals to be transmitted. The particular design of the communication subsystem is dependent upon the communication network and associated wireless communications protocols with which the device is intended to operate.

The electronic device 852 includes a microprocessor 802 that controls the overall operation of the electronic device 852. The microprocessor 802 interacts with the above described communications subsystem elements and also interacts with other device subsystems such as flash memory 806, random access memory (RAM) 804, auxiliary input/output (I/O) device 838, data port 828, display 834, keyboard 836, speaker 832, microphone 830, a short-range communications subsystem 820, a power subsystem 822, and any other device subsystems.

A battery 824 is connected to a power subsystem 822 to provide power to the circuits of the electronic device 852. The power subsystem 822 includes power distribution circuitry for providing power to the electronic device 852 and also contains battery charging circuitry to manage recharging the battery 824. The power subsystem 822 includes a battery monitoring circuit that is operable to provide a status of one or more battery status indicators, such as remaining capacity, temperature, voltage, electrical current consumption, and the like, to various components of the electronic device 852.

The data port 828 of one example is a receptacle connector 104 or a connector that to which an electrical and optical data communications circuit connector 800 engages and mates, as described above. The data port 828 is able to support data communications between the electronic device 852 and other devices through various modes of data communications, such as high speed data transfers over an optical communications circuits or over electrical data communications circuits such as a USB connection incorporated into the data port 828 of some examples. Data port 828 is able to support communications with, for example, an external computer or other device.

Data communication through data port 828 enables a user to set preferences through the external device or through a software application and extends the capabilities of the device by enabling information or software exchange through direct connections between the electronic device 852 and external data sources rather then via a wireless data communication network. In addition to data communication, the data port 828 provides power to the power subsystem 822 to charge the battery 824 or to supply power to the electronic circuits, such as microprocessor 802, of the electronic device 852.

Operating system software used by the microprocessor 802 is stored in flash memory 806. Further examples are able to use a battery backed-up RAM or other non-volatile storage data elements to store operating systems, other executable programs, or both. The operating system software, device application software, or parts thereof, are able to be temporarily loaded into volatile data storage such as RAM 804. Data received via wireless communication signals or through wired communications are also able to be stored to RAM 804.

The microprocessor 802, in addition to its operating system functions, is able to execute software applications on the electronic device 852. A predetermined set of applications that control basic device operations, including at least data and voice communication applications, is able to be installed on the electronic device 852 during manufacture. Examples of applications that are able to be loaded onto the device may be a personal information manager (PIM) application having the ability to organize and manage data items relating to the device user, such as, but not limited to, e-mail, calendar events, voice mails, appointments, and task items.

Further applications may also be loaded onto the electronic device 852 through, for example, the wireless network 850, an auxiliary I/O device 838, Data port 828, short-range communications subsystem 820, or any combination of these interfaces. Such applications are then able to be installed by a user in the RAM 804 or a non-volatile store for execution by the microprocessor 802.

In a data communication mode, a received signal such as a text message or web page download is processed by the communication subsystem, including wireless receiver 812 and wireless transmitter 810, and communicated data is provided the microprocessor 802, which is able to further process the received data for output to the display 834, or alternatively, to an auxiliary I/O device 838 or the Data port 828. A user of the electronic device 852 may also compose data items, such as e-mail messages, using the keyboard 836, which is able to include a complete alphanumeric keyboard or a telephone-type keypad, in conjunction with the display 834 and possibly an auxiliary I/O device 838. Such composed items are then able to be transmitted over a communication network through the communication subsystem.

For voice communications, overall operation of the electronic device 852 is substantially similar, except that received signals are generally provided to a speaker 832 and signals for transmission are generally produced by a microphone 830. Alternative voice or audio I/O subsystems, such as a voice message recording subsystem, may also be implemented on the electronic device 852. Although voice or audio signal output is generally accomplished primarily through the speaker 832, the display 834 may also be used to provide an indication of the identity of a calling party, the duration of a voice call, or other voice call related information, for example.

Depending on conditions or statuses of the electronic device 852, one or more particular functions associated with a subsystem circuit may be disabled, or an entire subsystem circuit may be disabled. For example, if the battery temperature is low, then voice functions may be disabled, but data communications, such as e-mail, may still be enabled over the communication subsystem.

A short-range communications subsystem 820 provides for data communication between the electronic device 852 and different systems or devices, which need not necessarily be similar devices. For example, the short-range communications subsystem 820 includes an infrared device and associated circuits and components or a Radio Frequency based communication module such as one supporting Bluetooth® communications, to provide for communication with similarly-enabled systems and devices, including the data file transfer communications described above.

A media reader 860 is able to be connected to an auxiliary I/O device 838 to allow, for example, loading computer readable program code of a computer program product into the electronic device 852 for storage into flash memory 806. One example of a media reader 860 is an optical drive such as a CD/DVD drive, which may be used to store data to and read data from a computer readable medium or storage product such as computer readable storage media 862. Examples of suitable computer readable storage media include optical storage media such as a CD or DVD, magnetic media, or any other suitable data storage device. Media reader 860 is alternatively able to be connected to the electronic device through the Data port 828 or computer readable program code is alternatively able to be provided to the electronic device 852 through the wireless network 850.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A method of improving doctor and patient communication, comprising:
   electronically transmitting a series of questions to a computing device of the patient;
   electronically receiving answers to the questions, provided by the patient, from the computing device of the patient, by a computer server;
   executing software stored on non-transitory media connected to the computer server, the software configured for analyzing the answers to the questions to determine if a state of health of the patient is serious and requires immediate attention of the doctor; and
   if the software determines the state of health is serious, transmitting an alert, using the server, to a computing device of the doctor; and
   wherein a determined state of health of serious corresponds to a third state of health, the software further configured to analyze the answers to the questions to determine if a first state of health of the patient is below a predetermined threshold corresponding to a satisfactory state, or a second state of health of the patient is between the thresholds of the first and third states of health corresponding to a worsening state of health.

2. The method of claim 1, further including electronically transmitting the received answers from the server to the computing device of the doctor.

3. The method of claim 1, wherein the computing device of the doctor is configured to execute software stored on non-transitory media, the software configured to display a visible alert, upon a display of the computing device of the doctor, in a form of a series of different colored lights to indicate a state of health of the patient corresponding to each of the third, second, and first states of health, respectively;
   the method further comprising indicating, using the visible alert to display a colored light corresponding to the determined state of health of the patient.

4. The method of claim 1, wherein the computing device of the doctor is configured to execute software stored on non-transitory media, the software configured to display a visible alert, upon a display of the computing device of the doctor, in the form of red, yellow, and green lights, to indicate a state of health of the patient corresponding to the third, second, and first states of health, respectively;
   the method further comprising indicating, using the visible alert, a red, yellow, or green light corresponding to the determined state of health of the patient.

5. The method of claim 1, wherein the computing device of the patient is configured to execute software stored on non-transitory media, the software configured to display a visible alert, upon a display of the computing device of the patient, in a form of red, yellow, and green lights, to indicate a state of health of the patient corresponding to the third, second, and first states of health, respectively;
   the method further comprising indicating, using the visible alert, a red, yellow, or green light corresponding to a current state of health of the patient.

6. The method of claim 1, wherein at least one of the computing device of the patient or the doctor is configured to execute software stored on non-transitory media, the software configured to display a visible alert, upon a display of the computing device of the patient or doctor, in the form of traffic light having red, yellow, and green lights, to indicate a state of health of the patient corresponding to the third, second, and first states of health, respectively;
   the method further comprising indicating, using the traffic light visible alert, a red, yellow, or green light corresponding to a current state of health of the patient.

7. The method of claim 1, wherein the software is further configured to generate reports for the patient and the doctor based upon the analysis of the answers to the questions; and
   the method further includes generating the reports for the patient and the doctor.

8. The method of claim 7, wherein the report for the patient and the doctor are different.

9. The method of claim 1, wherein the software is further configured to generate a report for the doctor, the report based upon the analysis of the answers to the questions, the report further including information not provided by the patient that is relevant to the analyzed state of the patient;
   the method further including transmitting the generated report to the doctor.

10. The method of claim 1, wherein the computing device of the patient is configured to execute software stored on non-transitory media, the software configured to prompt the patient to answer a subset of questions of the series of questions based on previous answers to questions of the series of questions;
    the method further including prompting the patient to answer the subset of questions.

11. The method of claim 1, wherein the computing device of the doctor is configured to execute software stored on non-transitory media, the software configured to generate a series of questions responsive to the received answers and data input from the doctor;
    the method further including generating the series of questions and transmitting the generated series of questions to the patient.

12. The method of claim 1, wherein the computing device of the doctor is configured to execute software stored on non-transitory media, the software configured to display, upon a display of the computing device of the doctor, information pertaining to contacting the patient;
    the method further including displaying the information pertaining to contacting the patient when the state of health of the patient is serious.

13. The method of claim 1, wherein the series of questions includes questions pertaining to at least one of a family life of the patient; a job and workplace of the patient; and an engagement by the patient in sport and exercise.

14. The method of claim 1, wherein the series of questions includes questions pertaining to at least one of side effects of any current medications of the patient; and allergies of the patient.

15. The method of claim 1, wherein the series of questions include questions pertaining to physical symptoms of the patient.

16. The method of claim 1, wherein the software is further configured to generate statistics relevant to the answers to the questions, the statistics indicating a state of health of the patient relative to a population of a plurality of patients with similar symptoms;
the method further including communicating the statistics to the patient using the computing device of the patient.

17. A method of improving doctor and patient communication, comprising:
electronically transmitting a series of questions to a computing device of the patient;
electronically receiving answers to the questions from the computing device of the patient by a computer server;
executing software stored on non-transitory media connected to the computer server, the software configured for analyzing the answers to the questions to—
determine if a state of health of the patient is serious and requires immediate attention of the doctor, and
determine a new series of questions to be transmitted to a computing device of the patient, the new series of questions derived from the received answers to question; and
if the software determines the state of health is serious, transmitting an alert, using the server, to a computing device of the doctor.

18. The method of claim 17, wherein at least one of the computing device of the patient or the doctor is configured to execute software stored on non-transitory media, the software configured to display a visible alert, upon a display of the computing device of the patient or doctor, in a form of a series of at least three different colored lights, to indicate a state of health of the patient corresponding to the serious state of health of the patient, a worsening state of health of the patient, and a non-serious state of health of the patient, respectively;
the method further comprising indicating, using the visible alert, a colored light corresponding to the determined state of health of the patient.

19. A system for improving doctor and patient communication, comprising:
a computer server configured to execute software stored on non-transitory media, the software configured for:
electronically receiving answers to questions provided by the patient, from a computing device of the patient;
executing software stored on non-transitory media connected to the computer server, the software configured for analyzing the answers to the questions to determine if a state of health of the patient is serious and requires immediate attention of the doctor; and
if the software determines the state of health is serious, transmitting an alert, using the server, to a computing device of the doctor; and
wherein the computing device of the doctor is configured to execute software stored on non-transitory media, the software configured to display, upon a display of the computing device of the doctor, information pertaining to contacting the patient when the state of health of the patient is serious.

20. The method of claim 19, wherein a determined state of health of serious corresponds to a third state of health, the software further configured to analyze the answers to the questions to determine if a first state of health of the patient is below a predetermined threshold corresponding to a satisfactory state, or a second state of health of the patient is between the thresholds of the first and third states of health corresponding to a worsening state of health.

* * * * *